US012631539B1

(12) United States Patent
Zhou et al.

(10) Patent No.: US 12,631,539 B1
(45) Date of Patent: May 19, 2026

(54) SINGLE-HOLE MULTI-STAGE PORE WATER PRESSURE OBSERVATION DEVICE AND INSTALLATION METHOD THEREOF

(71) Applicants: INSTITUTE OF MECHANICS, CHINESE ACADEMY OF SCIENCES, Beijing (CN); Zhejiang Natural Resources Group Spatial Information Co., Ltd, Hangzhou (CN)

(72) Inventors: Xinxing Zhou, Hangzhou (CN); Xiaoyu Liu, Beijing (CN); Fuping Wang, Hangzhou (CN); Haiqian Yu, Hangzhou (CN); Pengfei Weng, Hangzhou (CN); Kai Huang, Hangzhou (CN)

(73) Assignees: INSTITUTE OF MECHANICS, CHINESE ACADEMY OF SCIENCES, Beijing (CN); Zhejiang Natural Resources Group Spatial Information Co., Ltd, Hangzhou (CN)

( * ) Notice: Subject to any disclaimer, the term of this patent is extended or adjusted under 35 U.S.C. 154(b) by 0 days.

(21) Appl. No.: 19/452,489

(22) Filed: Jan. 19, 2026

Related U.S. Application Data

(63) Continuation of application No. PCT/CN2024/137401, filed on Dec. 6, 2024.

(30) Foreign Application Priority Data

Nov. 5, 2024 (CN) .......................... 202411569147.2

(51) Int. Cl.
*G01N 15/08* (2006.01)
*G01N 33/24* (2006.01)
(52) U.S. Cl.
CPC ......... *G01N 15/0806* (2013.01); *G01N 33/24* (2013.01)

(58) Field of Classification Search
CPC ........................... G01N 15/0806; G01N 33/24
See application file for complete search history.

(56) References Cited

U.S. PATENT DOCUMENTS

| | | | | |
|---|---|---|---|---|
| 3,374,664 | A | * | 3/1968 | Lefelhocz .......... G01N 15/0806 73/706 |
| 4,453,401 | A | * | 6/1984 | Sidey .................... G01L 9/0001 73/754 |

(Continued)

FOREIGN PATENT DOCUMENTS

| | | |
|---|---|---|
| CN | 103195045 A | 7/2013 |
| CN | 205617348 U | 10/2016 |

(Continued)

OTHER PUBLICATIONS

Office Action received in corresponding Chinese patent application No. 202411569147.2, dated Jun. 6, 2025, 10 pages.

(Continued)

*Primary Examiner* — Eric S. McCall
(74) *Attorney, Agent, or Firm* — Cooper Legal Group, LLC

(57) ABSTRACT

The present application relates to a single-hole multi-stage pore water pressure observation device and an installation method thereof. The single-hole multi-stage pore water pressure observation device includes: a plurality of digital piezometer probe assemblies arranged in a monitoring borehole from bottom to top, an inter-stage seepage-isolation cylinder assembly connected between two adjacent digital piezometer probe assemblies, and a watertight connector assemblies configured to connect the adjacent digital piezometer probe assemblies to the inter-stage seepage-isolation cylinder assembly, wherein each digital piezometer probe assembly includes a hollow water-permeable cylinder, a pore water pressure gauge assembly disposed in the water-permeable cylinder, a high-permeability material (Continued)

filled between an inner wall of the water-permeable cylinder and the pore water pressure gauge assembly, and water-permeable geotextile wrapped around the high-permeability material; and a multi-core cable is electrically connected between adjacent pore water pressure gauge assemblies.

10 Claims, 10 Drawing Sheets

(56)                    References Cited

U.S. PATENT DOCUMENTS

| | | | | |
|---|---|---|---|---|
| 5,076,392 A | * | 12/1991 | Koenig ................. | G01N 33/24 |
| | | | | 175/171 |
| 5,804,715 A | * | 9/1998 | Bennett ................... | E21B 47/06 |
| | | | | 73/866.5 |
| 2018/0119542 A1 | | 5/2018 | Wayne et al. | |

FOREIGN PATENT DOCUMENTS

| | | | |
|---|---|---|---|
| CN | 110685733 | A | 1/2020 |
| CN | 213875362 | U | 8/2021 |
| CN | 216559472 | U | 5/2022 |
| CN | 216746644 | U | 6/2022 |
| CN | 115807638 | A | 3/2023 |
| CN | 115928684 | A | 4/2023 |
| CN | 118088223 | A | 5/2024 |
| CN | 119555273 | A | 3/2025 |
| KR | 20240147799 | A | 10/2024 |

OTHER PUBLICATIONS

International Search Report received in corresponding International patent application No. PCT/CN2024/137401, mailed Jul. 3, 2025, 10 pages.

* cited by examiner

SINGLE-HOLE MULTI-STAGE PORE WATER PRESSURE OBSERVATION DEVICE AND INSTALLATION METHOD THEREOF

CROSS-REFERENCE TO RELATED APPLICATIONS

The present application is a continuation application of PCT application No. PCT/CN2024/137401, filed on Dec. 6, 2024, which claims priority to Chinese patent application No. 202411569147.2, filed on Nov. 5, 2024. The entireties of PCT application No. PCT/CN2024/137401 and Chinese patent application No. 202411569147.2 are hereby incorporated by reference herein and made a part of this specification.

TECHNICAL FIELD

The present application relates to the technical field of pore water pressure monitoring, and particularly to a single-hole multi-stage pore water pressure observation device and an installation method thereof.

BACKGROUND ART

Pore water pressure is pressure exerted by water present in soil, rock, or other porous media. It has a significant impact on mechanical properties and stability of geotechnical masses. Therefore, pore water pressure observation has become a major monitoring component in geotechnical engineering, and provides important data support for the analysis of deformation and stability of geotechnical masses.

At present, a dedicated instrument for pore water pressure observation is a pore water pressure gauge, also referred to as a piezometer. During use, a borehole needs to be drilled and the piezometer needs to be installed and embedded in the borehole. The embedding quality of the piezometer directly affects subsequent observation effects.

To more accurately grasp the variation pattern of pore water pressure inside geotechnical masses with respect to depth, numerous engineering projects require embedding multiple (i.e., multi-stage) piezometers at different soil layer depths. Compared with a traditional single-hole single-point arrangement scheme, the single-hole multi-stage arrangement scheme (i.e., multiple piezometers are densely installed within a single borehole) can not only effectively reduce the total number of boreholes and save project costs, but more importantly, all observation data originates from the same monitoring cross-section, providing greater correlation and consistency between data from different observation points.

In the implementation of the single-hole multi-stage arrangement scheme, firstly, it is necessary to ensure that piezometers at various depths laterally communicate with corresponding rock and soil layers, so that pore water pressure in rock and soil of the same layer can be transmitted to the piezometer with minimal pressure gradient loss. A current process involves filling sand around the piezometers, so that sand particles come into contact with a borehole wall of rock and soil, thereby effectively transmitting the pore water pressure. Secondly, given that the pore water pressure varies across formations at different depths, it is also necessary to ensure vertical isolation between the piezometers to prevent water cross-flow between upper and lower piezometers. To this end, it is necessary to fill a material such as clay between the upper and lower piezometers, and adopt a step-by-step embedding and layer-by-layer isolation method to ensure independent operation of the piezometers at various depths.

The traditional step-by-step and layer-by-layer embedding method involves complex processes, cumbersome operational procedures and long time consumption; moreover, in the case of complex geological conditions such as deep-hole operations and weak soil layers, precise placement of the backfill material becomes particularly difficult to control. This directly causes difficulties in constructing an effective seepage filter layer around probes of pore water pressure gauges, such that sealing between probes of upper and lower pore water pressure gauges is difficult to achieve or is inadequate, thereby compromising installation quality and failing to ensure the accuracy of measurement data.

SUMMARY

In view of this, the present application provides a single-hole multi-stage pore water pressure observation device and an installation method thereof to simplify complex installation and embedding procedures of single-hole multi-stage pore water pressure gauges and reduce operational time, while addressing the issue of limited measurement accuracy of pore water pressure data caused by challenges in backfill material placement.

In a first aspect, the present application provides a single-hole multi-stage pore water pressure observation device, which adopts the following technical solution:

A single-hole multi-stage pore water pressure observation device includes a plurality of digital piezometer probe assemblies arranged at intervals in a monitoring borehole from bottom to top, an inter-stage seepage-isolation cylinder assembly connected between two adjacent digital piezometer probe assemblies, and watertight connector assemblies configured to connect the adjacent digital piezometer probe assemblies to the inter-stage seepage-isolation cylinder assembly, wherein each digital piezometer probe assembly includes a slender hollow water-permeable cylinder, a pore water pressure gauge assembly disposed in the water-permeable cylinder, a high-permeability material filled in gaps between an inner wall of the water-permeable cylinder and the pore water pressure gauge assembly, and a water-permeable geotextile wrapped around the high-permeability material; and a multi-core cable is electrically connected between adjacent pore water pressure gauge assemblies, and the multi-core cable passes through the inter-stage seepage-isolation cylinder assembly between the adjacent pore water pressure gauge assemblies.

In the single-hole multi-stage pore water pressure observation device according to the present application, multi-stage digital piezometer probe assemblies can be arranged at high density in a single borehole, e.g., one digital piezometer probe assembly is arranged every 3 meters. This can not only effectively reduce the number of monitoring boreholes and save project costs, but also all observation data originates from the same monitoring cross-section, providing greater correlation and consistency between data from different observation points.

Traditional pore water pressure gauges adopt a discrete wiring mode, in which each probe requires an independent cable, which means that installing n probes requires n cables, leading to high costs and cumbersome installation. In the present application, through digitalization of the digital piezometer probe assemblies and a bus design mode, all probes in a single borehole share one multi-core cable (two cores for power supply, and two cores for data transmission), thereby substantially reducing observation costs and simplifying the installation procedure.

Optionally, the inter-stage seepage-isolation cylinder assembly includes one section of seepage-isolation cylinder or a plurality of sections of seepage-isolation cylinders connected in series;

each seepage-isolation cylinder includes a central tube and a grid cage which are concentrically arranged from inside to outside, and a water-swellable material wrapped in a water-soluble film is filled between the central tube and the grid cage; and the multi-core cable extends out from both ends of the central tube and is connected to two adjacent pore water pressure gauge assemblies, respectively.

Optionally, a side wall of the water-permeable cylinder is defined with a plurality of water-permeable holes, and upper and lower ends of the water-permeable cylinder are provided with cylinder covers, each cylinder cover being provided with an adapter tube configured to be connected to a first end of a watertight connector assembly; and the multi-core cable connected to the pore water pressure gauge assembly sequentially passes through the adapter tube and extends into the inter-stage seepage-isolation cylinder assembly, and an inner wall of the adapter tube is provided with potting adhesive.

Optionally, the watertight connector assembly includes a threaded sleeve with upper and lower openings and silicone annular gaskets;

the threaded sleeve is internally provided with a transverse plate which divides the threaded sleeve into an upper chamber and a lower chamber, with a hole being formed at a center of the transverse plate to allow the multi-core cable to pass through; and the silicone annular gaskets are laid on both sides of the transverse plate respectively, and the upper chamber and the lower chamber on both sides of the transverse plate are respectively configured for threaded connection with the adapter tube and the inter-stage seepage-isolation cylinder assembly.

Optionally, the pore water pressure gauge assembly includes a package housing, a small locknut, a large locknut, an acquisition circuit board, a pore water pressure sensor and a signal wire thereof which are electrically connected to the acquisition circuit board, and a probe multi-core cable electrically connected to the acquisition circuit board; and part of the probe multi-core cable, the signal wire, and the acquisition circuit board are all located within the package housing; the small locknut is configured to seal off a part where the signal wire extends out of the package housing; and the large locknut is configured to seal off a part where the probe multi-core cable extends out of the package housing.

Optionally, the acquisition circuit board includes:

an MCU microcontroller integrated with a storage module;

an excitation and frequency sweeping module, a signal processing module and a temperature acquisition module which are all electrically connected to the MCU microcontroller; and a bus communication module and a power supply module which are both electrically connected to the MCU microcontroller; and the pore water pressure sensor is electrically connected to the excitation and frequency sweeping module, the signal processing module and the temperature acquisition module.

Optionally, the high-permeability material is medium-coarse sand, the water-swellable material is water-swellable resin, and the acquisition circuit board is externally sealed and encapsulated with epoxy resin.

Optionally, the plurality of digital piezometer probe assemblies, the seepage-isolation cylinder and the watertight connector assemblies are all integrally prefabricated.

Optionally, in a case where the inter-stage seepage-isolation cylinder assembly includes the plurality of sections of seepage-isolation cylinders connected in series, the watertight connector assembly is connected between the seepage-isolation cylinders; and each watertight connector assembly further includes a fastening screw, and the threaded sleeve is defined with a threaded hole corresponding to the fastening screw.

In a second aspect, the present application provides an installation method for the single-hole multi-stage pore water pressure observation device.

In summary, the present application achieves at least one of the following beneficial technical effects.

The present application integrates a backfill material into a manufacturing procedure of a pore water pressure observation device, achieving integrated design, manufacture and installation of the observation device and the backfill material. Specifically, a coarse sand layer is directly prefabricated inside the water-permeable cylinder, and a novel material combination of water-swellable material and water-soluble film is introduced, and formed in a chamber of the seepage-isolation cylinder in place of traditional bentonite or highly disintegratable clay balls, forming an efficient borehole sealing layer. This design concept changes the traditional construction mode, eliminating the need for an additional backfill material during on-site installation and greatly simplifying the installation procedure. More importantly, using a factory-based manufacturing mode can ensure standardization and normalization of embedding and installation, and effectively guarantee installation quality, making pore water pressure monitoring data more accurate and reliable, providing solid technical support for engineering monitoring.

DETAILED DESCRIPTION

The present application is further described in detail below with reference to FIGS. 1 to 10.

Embodiments of the present application discloses a single-hole multi-stage pore water pressure observation device.

Figure 1:
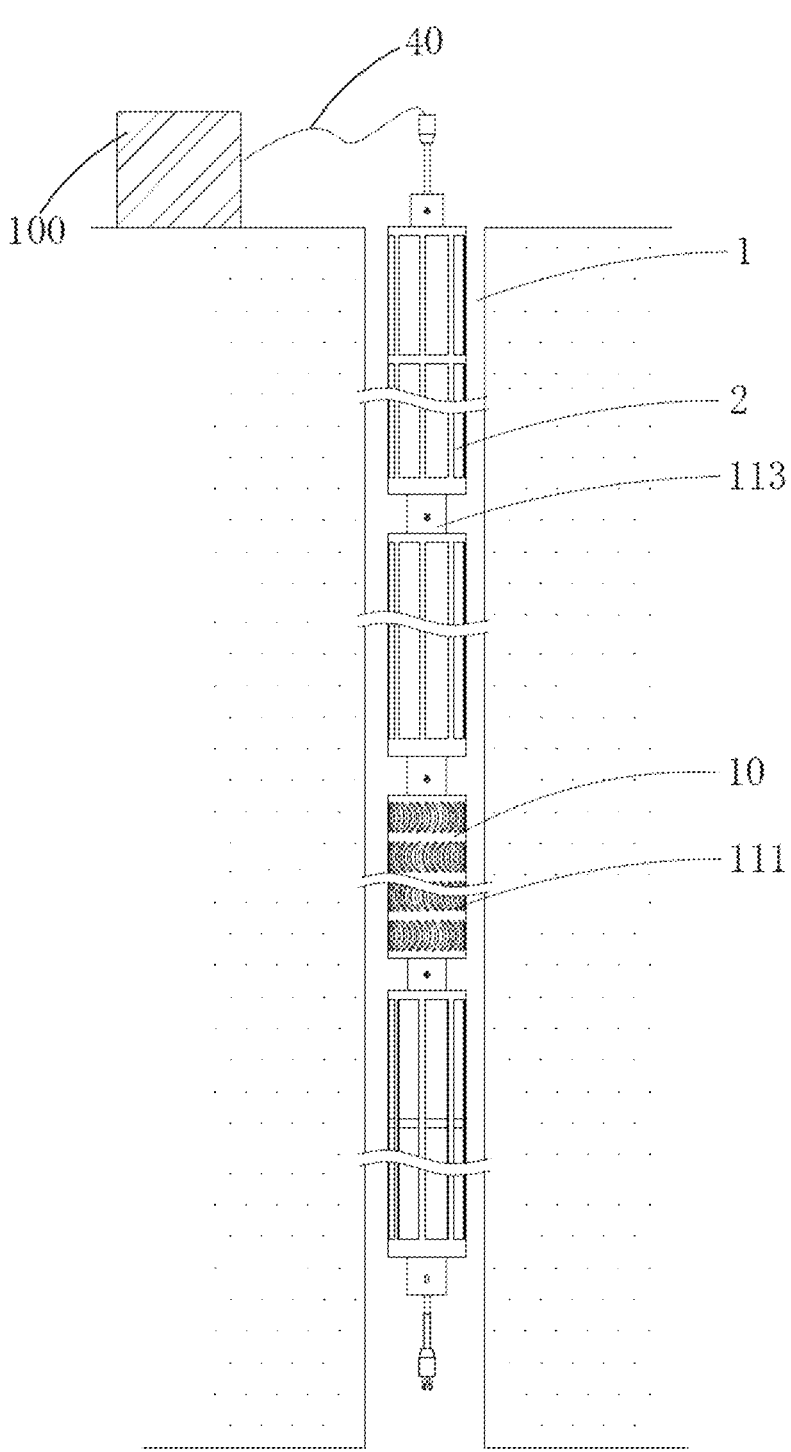
FIG. 1 is a schematic overall structural view of a single-hole multi-stage pore water pressure observation device according to the present application.
Figure 2:
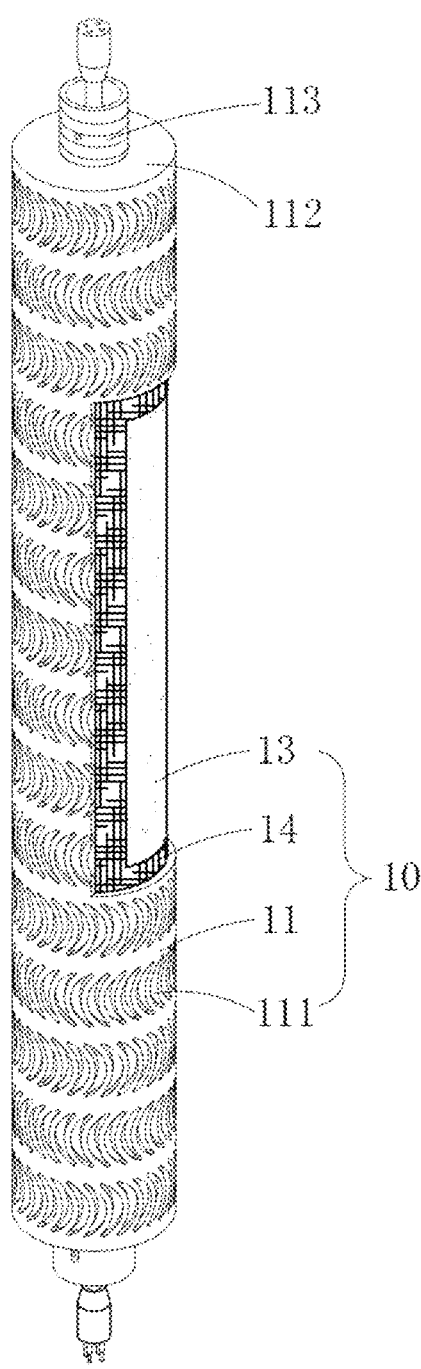
FIG. 2 is a schematic structural view of a digital piezometer probe assembly according to the present application.
Figure 3:
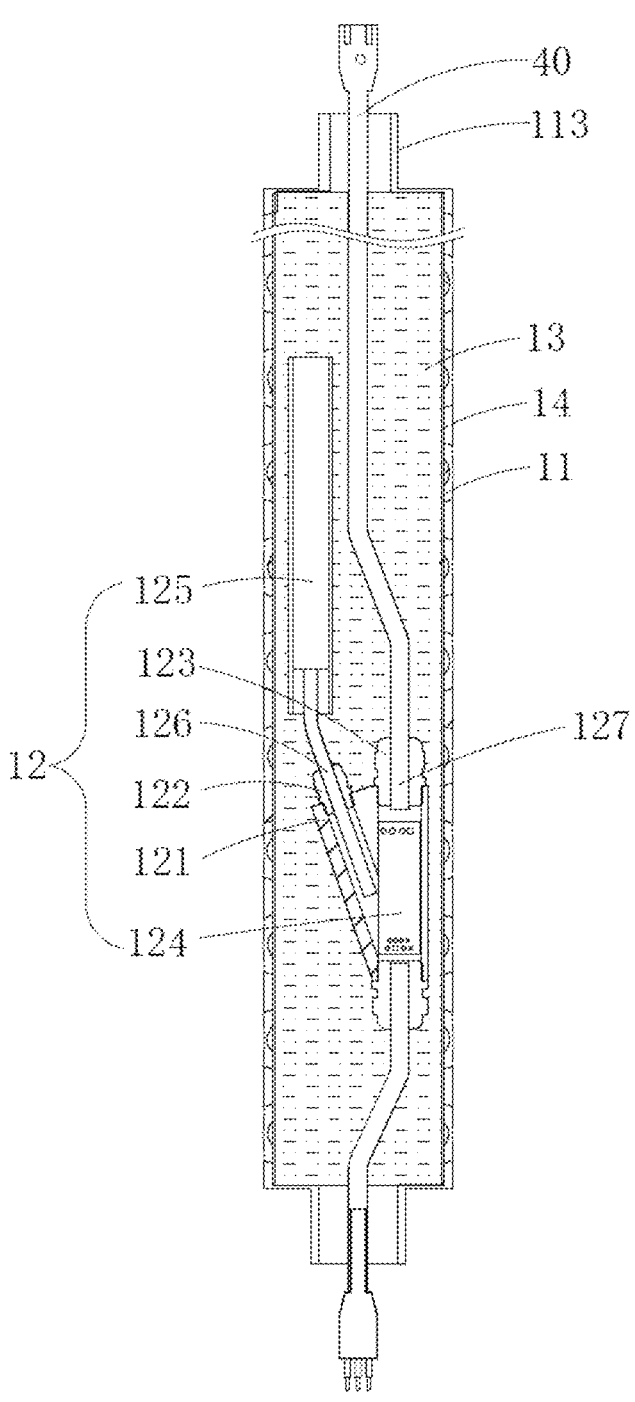
FIG. 3 is a cross-sectional view of the digital piezometer probe assembly according to the present application.

Referring to FIGS. 1, 2 and 3, a monitoring borehole 1 is drilled at a site to be tested, and the single-hole multi-stage pore water pressure observation device includes a plurality of digital piezometer probe assemblies 10 (only one digital piezometer probe assembly 10 is illustrated in the figures) arranged at intervals from an opening to a bottom of the monitoring borehole 1. The plurality of digital piezometer probe assemblies 10 together form a linearly distributed pore water pressure observation array, which allows real-time monitoring of a variation pattern of pore water pressure with respect to different depths along the same monitoring cross-section. Electrical connection is implemented via a multi-core cable 40 between a first-stage digital piezometer probe assembly 10 and a ground acquisition station 100, and between adjacent digital piezometer probe assemblies 10.

A distance between two adjacent digital piezometer probe assemblies 10 is not limited, and an inter-stage seepage-isolation cylinder assembly 2 is connected therebetween. The adjacent digital piezometer probe assemblies 10 are connected to the inter-stage seepage-isolation cylinder assembly 2 through watertight connector assemblies 30 (refer to FIGS. 7*a* and 7*b*).

Each digital piezometer probe assembly 10 includes a long tubular, hollow water-permeable cylinder 11. A diameter of the water-permeable cylinder 11 is slightly smaller than a bore diameter of the monitoring borehole 1. A pore water pressure gauge assembly 12 for monitoring pore water pressure is disposed in the water-permeable cylinder 11. On a side wall of the water-permeable cylinder 11, a plurality of crescent-shaped water-permeable holes 111 are defined at uniform intervals, for allowing water from a formation to enter the water-permeable cylinder 11. A high-permeability material 13 is filled in gaps between an inner wall of the water-permeable cylinder 11 and the pore water pressure gauge assembly 12. The high-permeability material 13 is medium-coarse sand, with water-permeable geotextile 14 wrapped around the exterior of the high-permeability material 13. The water-permeable geotextile 14 is nonwoven geotextile.

FIG. 2 illustrates a case where the water-permeable geotextile 14 is directly wrapped around the high-permeability material 13, but this is not limiting. Of course, the water-permeable geotextile 14 may also be wrapped around an exterior of the water-permeable cylinder 11, thereby indirectly wrapped around the high-permeability material 13.

Upper and lower ends of the water-permeable cylinder 11 are provided with cylinder covers 112. The cylinder covers

112 may be in threaded connection with or welded to the water-permeable cylinder 11. Each cylinder cover 112 has a stainless steel adapter tube 113 welded thereon, which is configured to be connected to a first end of a watertight connector assembly 30. The multi-core cable 40 connected to the pore water pressure gauge assembly 12 sequentially passes through the cylinder cover 112 and the adapter tube 113. An inner wall of the adapter tube 113 is provided with potting adhesive to seal off the stainless steel adapter tube 113 and prevent seepage of the high-permeability material 13.

The pore water pressure gauge assembly 12 includes a package housing 121, a small locknut 122, a large locknut 123, an acquisition circuit board 124, a pore water pressure sensor 125 and a signal wire 126 thereof which are electrically connected to the acquisition circuit board 124, and a probe multi-core cable 127 electrically connected to the acquisition circuit board 124. The probe multi-core cable 127 is connected to the multi-core cable 40 outside the package housing 121.

The probe multi-core cable 127, part of the signal wire 126, and the acquisition circuit board 124 are all located within the package housing 121. The small locknut 122 is configured to seal off an interface where the signal wire 126 extends out of the package housing 121. The large locknut 123 is configured to seal off an interface between the probe multi-core cable 127 and the package housing 121. The package housing 121, together with the small locknut 122 and the large locknut 123, forms a closed chamber, ensuring safety protection of electronic components within the acquisition circuit board 124 and cable interfaces in a harsh environment.

The pore water pressure sensor 125 is a commercially available high-precision vibrating-wire pore water pressure gauge. The multi-core cable 40 adopts multi-core signal wires, with four cores utilized. Two cores are power supply cables configured to supply power to the pore water pressure sensor 125 and the acquisition circuit board 124. Two cores are data transmission buses configured to transmit data between the acquisition circuit board 124 and the ground acquisition station 100.

Figure 4:
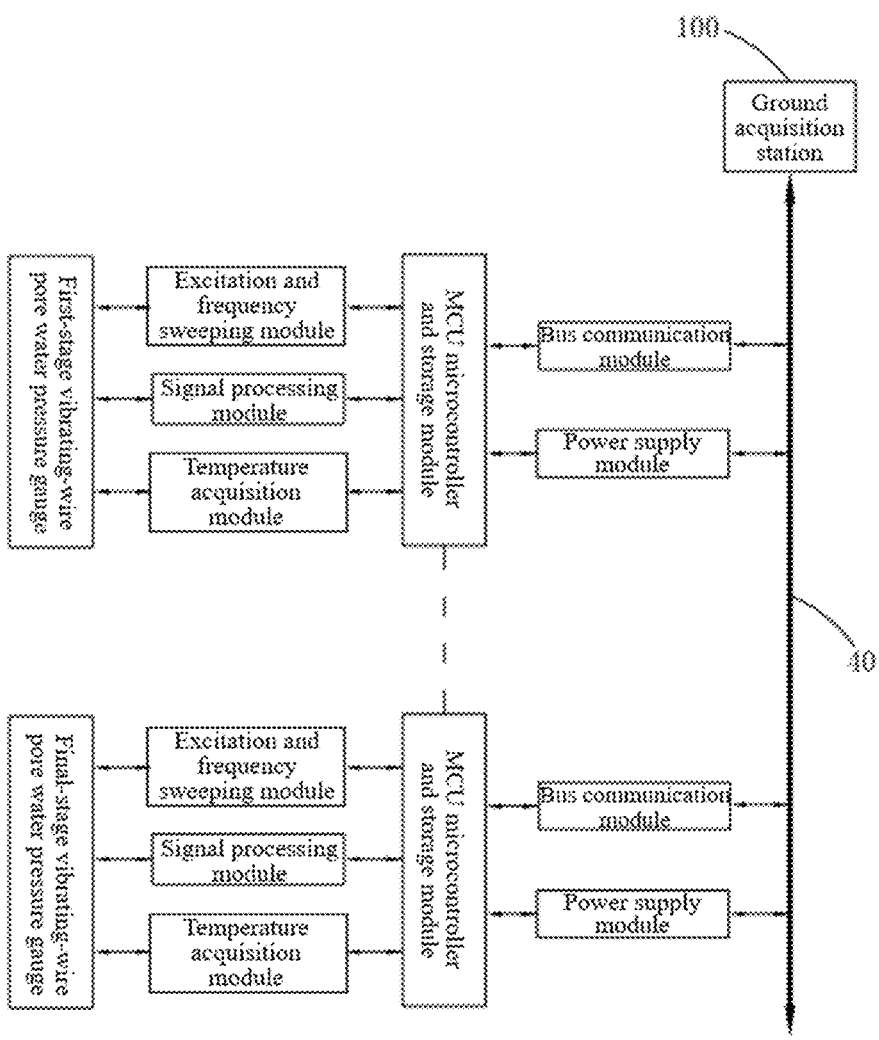
FIG. 4 is a schematic view of circuit modules of a single-hole multi-stage pore water pressure observation device according to the present application.

Further referring to FIG. 4, the acquisition circuit board 124 includes an MCU microcontroller integrated with a storage module. The MCU microcontroller can perform calculations on received data. The storage module is configured to store data. The MCU microcontroller is electrically connected to an excitation and frequency sweeping module, a signal processing module, a temperature acquisition module, a bus communication module, and a power supply module, respectively. The MCU microcontroller and the storage module are composed of an STM32 single-chip microcomputer, a memory, and peripheral circuits thereof. By operating the excitation and frequency sweeping module, the signal processing module, the temperature acquisition module, and the bus communication module, the acquisition, storage, and uploading of pore water pressure and ambient temperature as well as the reception of and response to upper computer commands can be autonomously accomplished. The excitation and frequency sweeping module is configured to perform excitation and frequency sweeping of the vibrating-wire pore water pressure gauge. The signal processing module is configured to perform filtering, amplifying, and ADC conversion on a vibrating-wire signal, and transmit a digitized vibrating-wire frequency to the MCU microcontroller. The temperature acquisition module is configured to acquire an ambient temperature signal of the vibrating-wire pore water pressure gauge, convert the ambient temperature signal into a digital quantity, and transmit the digital quantity to the MCU microcontroller. The bus communication module is connected to the data transmission buses in the multi-core cable 40, and configured to implement data interaction between the MCU microcontroller and the ground acquisition station 100. The power supply module is connected to the power supply cables in the multi-core cable 40, to supply power to the MCU microcontroller.

The acquisition circuit board 124 is mounted within the closed chamber formed by the package housing 121, the small locknut 122 and the large locknut 123, and is welded to the signal wire 126 of the pore water pressure sensor 125 and the multi-core cable 40, respectively, and sealed with epoxy resin for waterproofing. The small locknut 122 and the large locknut 123 respectively lock the signal wire 126 of the pore water pressure sensor 125 and the probe multi-core cable 127, ensuring stable cable connections and excellent waterproof performance.

The combination of the water-permeable geotextile 14, the stainless steel water-permeable cylinder 11 and the high-permeability material 13 can ensure unobstructed water seepage around the pore water pressure sensor 125.

Figure 5:
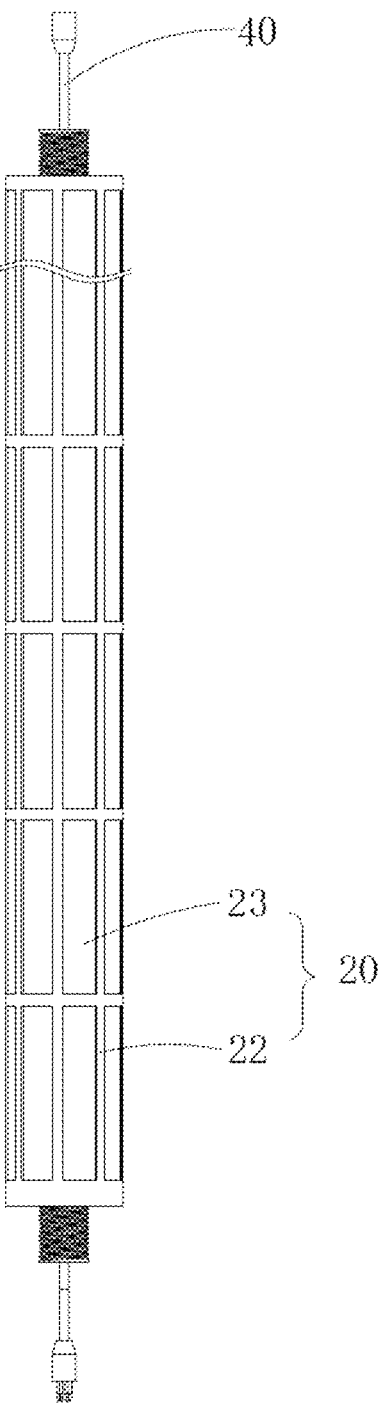
FIG. 5 is a schematic structural view of an inter-stage seepage-isolation cylinder assembly according to the present application.
Figure 6:
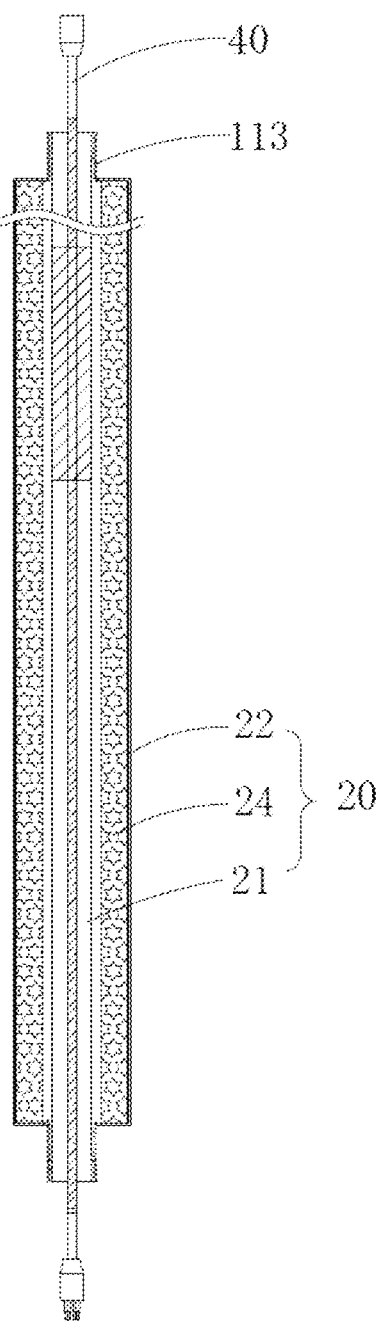
FIG. 6 is a cross-sectional view of the inter-stage seepage-isolation cylinder assembly according to the present application.

Referring to FIGS. 1, 5 and 6, the inter-stage seepage-isolation cylinder assembly 2 includes one section of seepage-isolation cylinder 20 or a plurality of sections of seepage-isolation cylinders 20 connected in series. FIG. 1 illustrates a case where the inter-stage seepage-isolation cylinder assembly 2 includes one section of seepage-isolation cylinder 20 or two sections of seepage-isolation cylinders 20 connected in series respectively. An inter-stage seepage-isolation cylinder assembly 2 below a digital piezometer probe assembly 10 includes one section of seepage-isolation cylinder 20, and an inter-stage seepage-isolation cylinder assembly 2 above the digital piezometer probe assembly 10 includes two sections of seepage-isolation cylinders 20. The length and number of the inter-stage seepage-isolation cylinder assembly 2 are determined according to monitoring design requirements. A customized example is as follows: each digital piezometer probe assembly 10 has a length of 0.6 m, and each seepage-isolation cylinder 20 has a length of 1.2 m; and one digital piezometer probe assembly 10 is assembled between every two sections of seepage-isolation cylinders 20, forming a layout mode of a digital piezometer probe array with an interval of 3 meters.

Each seepage-isolation cylinder 20 includes a central tube 21 and a grid cage 22 which are concentrically arranged from inside to outside. The multi-core cable 40 extends through the central tube 21 and is laid inside the central tube. An inner chamber of the central tube 21 is configured to allow the multi-core cable 40 to pass through, and is sealed with potting adhesive. A chamber between the central tube 21 and the grid cage 22 is an outer chamber, and configured to be filled with a water-swellable material 24. Before contact with water, the water-swellable material 24 is in a powder form and wrapped in a water-soluble film 23. Two ends of the multi-core cable 40 inside the central tube 21 are respectively connected with a watertight male connector and a watertight female connector, and two ends of the multi-core cable 40 on the pore water pressure gauge assembly 12 are also respectively connected with a watertight male connector and a watertight female connector.

The segments of the multi-core cable 40 in adjacent digital piezometer probe assemblies 10 are assembled to the segment of the multi-core cable 40 in the central tube 21 of the seepage-isolation cylinder 20 by means of plug-in connection between a watertight male connector and a watertight female connector, and the segments of the multi-core cable 40 in the central tubes 21 of two adjacent seepage-isolation cylinders 20 are also assembled to each other by means of plug-in connection between a watertight male connector and a watertight female connector.

The water-soluble film 23 is a film-like material that readily degrades upon contact with water, such as a water-soluble membrane. Small holes are formed in the water-soluble film 23 to facilitate the seepage of water within the monitoring borehole 1. When the water-soluble film 23 dissolves slowly, the seeping water can not only shorten swelling time of the water-swellable material 24 in contact with water, but also cause the water-swellable material 24 to rupture the water-soluble film 23 during swelling, thereby further accelerating a seepage-isolation process of the borehole.

An outer diameter of the grid cage 22 of the seepage-isolation cylinder 20 is the same as that of the water-permeable cylinder 11. An outer diameter of the central tube 21 is the same as that of the stainless steel adapter tube 113.

The water-swellable material 24 may be water-swellable resin. The water-swellable material 24 starts swelling hours after contact with water, and with a maximum swelling volume of 700 times, it can extend beyond the grid cage 22 and fully occupy an entire borehole space, forming a borehole sealing layer, thereby effectively preventing vertical communication and mutual seepage between adjacent digital piezometer probe assemblies 10.

Figure 7A:
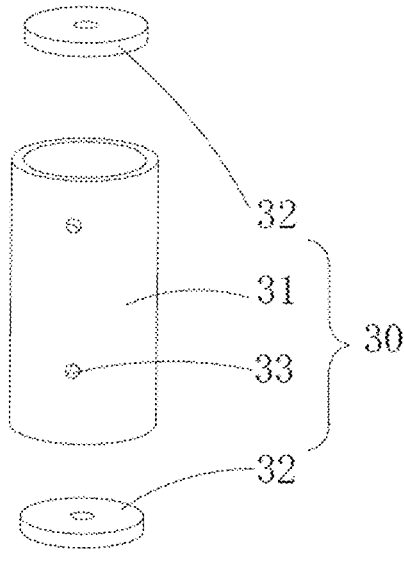
FIG. 7a is a schematic exploded structural view of a watertight connector assembly according to the present application.
Figure 7B:
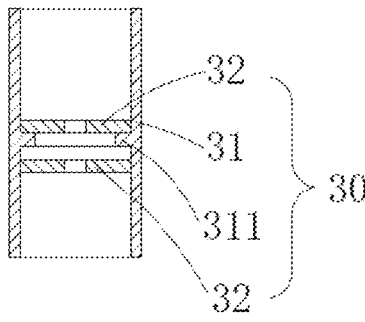
FIG. 7*b* is a combined structural cross-sectional view of the watertight connector assembly according to the present application.

Further referring to FIGS. 7a and 7b, external threads are formed at both ends of the central tube 21. The external threads are used to connect the watertight connector assemblies 30. Each watertight connector assembly 30 includes a threaded sleeve 31 with upper and lower openings and silicone annular gaskets 32. The threaded sleeve 31 is internally provided with a transverse plate 311 which divides the threaded sleeve into an upper chamber and a lower chamber.

A hole is formed at a center of the transverse plate 311 to allow the multi-core cable 40 to pass through. The silicone annular gaskets 32 are laid on both sides of the transverse plate 311 respectively, and the upper chamber and the lower chamber on both sides of the transverse plate 311 are respectively configured for threaded connection with the adapter tube 113 and the central tube 21 of the inter-stage seepage-isolation cylinder assembly 2. Specifically, one chamber is configured to allow insertion and threaded connection of the central tube 21 of the inter-stage seepage-isolation cylinder assembly 2, and the other chamber is configured to allow insertion and threaded connection of the adapter tube 113 on the cylinder cover 112 of the water-permeable cylinder 11. Upper and lower ends of the threaded sleeve 31 are both defined with threaded holes to allow insertion of fastening screws 33, and are respectively pressed against an outer wall of the adapter tube 113 and an outer wall of the central tube 21.

The silicone annular gaskets 32 serve as separation layers to prevent the water-swellable material 24 from intruding into gaps between the digital piezometer probe assembly 10 and a borehole wall during swelling of the water-swellable material in contact with water, and thereby affecting unobstructed water seepage around the digital piezometer probe assembly 10.

In a case where the inter-stage seepage-isolation cylinder assembly 2 includes the plurality of sections of seepage-isolation cylinders 20 connected in series, adjacent seepage-isolation cylinders 20 are also connected through the water-tight connector assembly 30 in the same manner as described above.

The single-hole multi-stage pore water pressure observation device adopts a factory-based integrated manufacturing process. Assembly of the plurality of digital piezometer probe assemblies 10 and welding and encapsulation of internal circuits thereof, assembly of units of the seepage-isolation cylinder 20 and routing and encapsulation of internal circuits thereof, and assembly of the watertight connector assemblies 30 are all performed in a factory in advance, simplifying a cumbersome on-site assembly procedure.

The entire multi-core cable 40 is divided into segments: cables in the water-permeable cylinders 11 and a cable in the seepage-isolation cylinder 20. The segments are respectively routed and encapsulated in inner cavities of the water-permeable cylinders 11 and the inter-stage seepage-isolation cylinder assembly 2, thereby avoiding friction damage to the cables caused by cable exposure during transportation and installation. The segments of cables at joints between the water-permeable cylinders 11 and the inter-stage seepage-isolation cylinder assembly 2 are assembled by means of plug-in connection between a watertight male connector and a watertight female connector. The watertight connector assemblies 30 are arranged at joints between the seepage-isolation cylinder 20 of each inter-stage seepage-isolation cylinder assembly 2 and the water-permeable cylinders 11. Plug-in assembly is performed during on-site installation, and waterproof performance is provided. In an unassembled state, a male end and a female end of the watertight connector assembly 30 are respectively protected by a protective cap and a protective plug.

Embodiments of the present application further disclose an installation method for the above-described single-hole multi-stage pore water pressure observation device.

Figure 8:
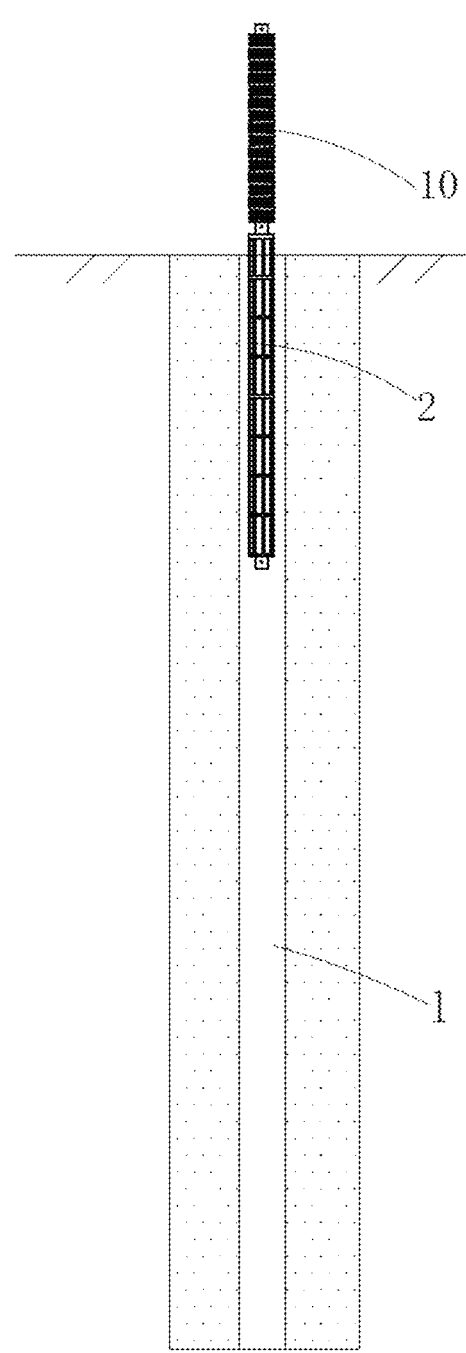
FIG. 8 is a schematic view of an initial installation state of the single-hole multi-stage pore water pressure observation device according to the present application.
Figure 9:
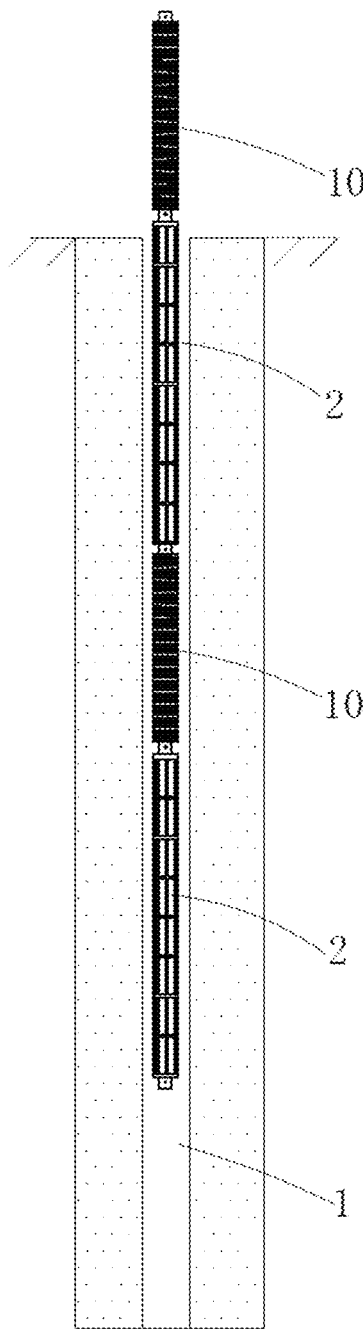
FIG. 9 is a schematic view of an in-installation state of the single-hole multi-stage pore water pressure observation device according to the present application.
Figure 10:
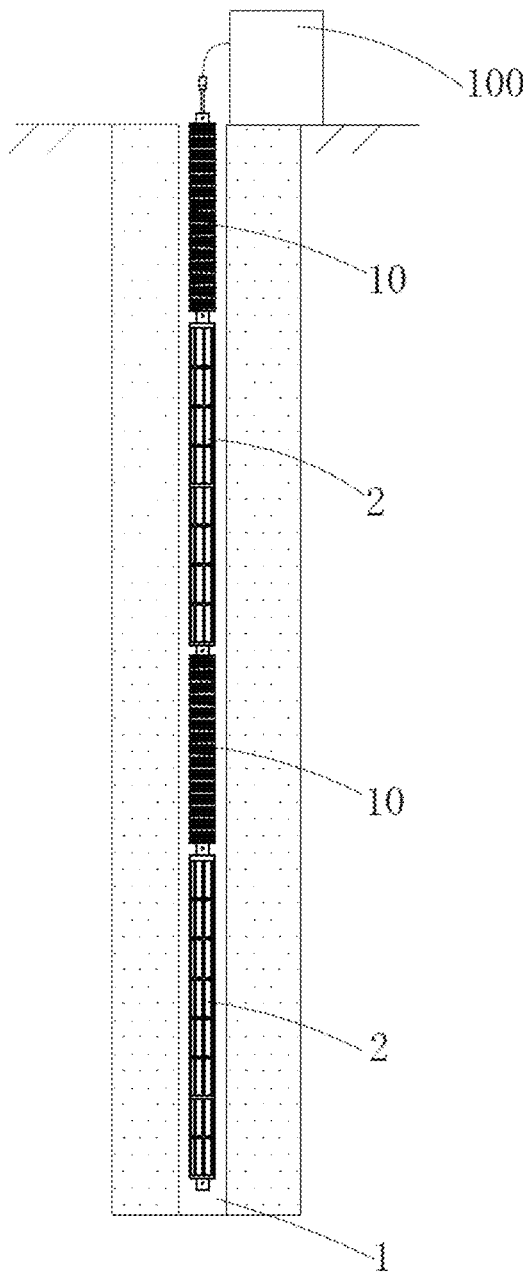
FIG. 10 is a schematic view of a post-installation state of the single-hole multi-stage pore water pressure observation device according to the present application.

Referring to FIGS. 8, 9 and 10, an installation method for the above-described single-hole multi-stage pore water pressure observation device includes the following steps:

S1: According to observation design requirements, a drilling rig is deployed to drill a borehole at a site to be tested, and a drilling casing is used to protect a borehole wall and prevent borehole collapse. When the borehole is drilled to a depth that is deeper than a designed depth by the length of one section of seepage-isolation cylinder 20, a drill pipe is pulled out, a temporary work platform is erected near a borehole opening, and all equipment and materials for installation are prepared.

S2: A single-hole multi-stage pore water pressure observation device is customized and transported in a disassembled state to the site. The number of digital piezometer probe assemblies 10, the length and number of inter-stage seepage-isolation cylinder assembly 2 between digital piezometer probe assemblies 10 at two adjacent stages are determined according to monitoring design requirements. A customized example is as follows: each digital piezometer probe assembly 10 has an overall length of 0.6 m, and each section of seepage-isolation cylinder 20 has a length of 1.2 m; and one digital piezometer probe assembly 10 is assembled between every two sections of seepage-isolation cylinders 20, forming a layout mode of a digital piezometer probe array with an interval of 3 meters.

S3: before embedding, all the digital piezometer probe assemblies 10 are soaked in clean water for more than 24 h on the ground to expel air from probes inside the digital piezometer probe assemblies 10.

S4: at the same time, before embedding, the seepage-isolation cylinders 20 in each inter-stage seepage-isolation cylinder assembly 2 are assembled on the ground. Connecting cylinder ends of the two adjacent seepage-isolation cylinders 20 are first butt-jointed by using a watertight connector assembly 30, and then rotationally connected by using an internal thread of a threaded sleeve 31 and pressed and fixed with a fastening screw 33. Segments of a multi-core cable 40 in central tubes 21 of the two adjacent seepage-isolation cylinders 20 are also assembled by means of plug-in connection between a watertight male connector and a watertight female connector.

S5: Using auxiliary devices such as a wellhead tool and a pull rope, the multi-stage digital piezometer probe assemblies 10 and the inter-stage seepage-isolation cylinder assemblies 2 are assembled and placed into a monitoring borehole 1 using a stage-by-stage installation method. Specifically, 1) a section of seepage-isolation cylinder 20 is selected as a bottom sealing layer, and the seepage-isolation cylinder 20 is bound with the pull rope, and then lowered into the borehole, leaving an end thereof above the borehole opening, and fixed with the wellhead tool. The pull rope is used to assist in installation, preventing a structure from falling into the borehole, and facilitating pulling out equipment when the structure is stuck in the borehole. 2) Using a watertight connector assembly 30, the seepage-isolation cylinder 20 is connected to a final-stage digital piezometer probe assembly 10 (containing a final-stage vibrating-wire pore water pressure gauge, as shown in FIG. 4) by means of a thread and pressed and fixed with a fastening screw 33. 3) The pull rope is slowly lowered, and the final-stage digital piezometer probe assembly 10 is placed into the monitoring borehole 1, leaving an end thereof above the borehole opening, and fixed with the wellhead tool. 4) The final-stage digital piezometer probe assembly 10 is connected to a watertight connector assembly 30 and to the next inter-stage seepage-isolation cylinder assembly 2, and then connected by means of a thread and pressed and fixed with a fastening screw 33. The connected inter-stage seepage-isolation cylinder assembly 2 is placed into the monitoring borehole 1, leaving an end thereof above the borehole opening, and fixed with the wellhead tool. 5) A penultimate-stage digital piezometer probe assembly 10 (containing a penultimate-stag vibrating-wire pore water pressure gauge) is further assembled. Segments of the multi-core cable 40 in adjacent digital piezometer probe assemblies 10 are assembled to a segment of the multi-core cable 40 in a central tube 21 of a seepage-isolation cylinder 20 by means of plug-in connection between a watertight male connector and a watertight female connector.

Assembly is continued in sequence until a first-stage digital piezometer probe assembly 10 (containing a first-stage vibrating-wire pore water pressure gauge, as shown in FIG. 4) and a corresponding inter-stage seepage-isolation cylinder assembly 2 and watertight connector assembly 30 are placed into the borehole.

S6: A ground acquisition station 100 is installed, and the working status of probes at all stages and the integrity of data transmission are commissioned and tested, ensuring that the probes function properly and that data transmission and clock synchronization are accurate and error-free.

S7: The casing is pulled out of the borehole, and the borehole is fully filled with water. Using a water-swellable material 24 that swells upon contact with water, a borehole sealing layer is formed between the digital piezometer probe assemblies 10 at the stages. This achieves mutual isolation of water pressures in formations where the digital piezometer probe assemblies 10 at the stages are located, preventing vertical communication and mutual seepage between the pore water pressure gauge assemblies 12 at the stages.

The above are preferred embodiments of the present application, which are not intended to limit the scope of protection of the present application. Therefore, any equivalent changes made based on the structure, shape, or principles of the present application shall be encompassed within the scope of protection of the present application.

LISTING OF REFERENCE SIGNS

1. Monitoring borehole;
10. Digital piezometer probe assembly;
11. Water-permeable cylinder;
111. Water-permeable hole;
112. Cylinder cover;
113. Adapter tube;
12. Pore water pressure gauge assembly;
121. Package housing;
122. Small locknut;
123. Large locknut;
124. Acquisition circuit board;
125. Pore water pressure sensor;
126. Signal wire;
127. Probe multi-core cable;
13. High-permeability material;
14. Water-permeable geotextile;
2. Inter-stage seepage-isolation cylinder assembly;
20. Seepage-isolation cylinder;
21. Central tube;
22. Grid cage;
23. Water-soluble film;
24. Water-swellable material;
30. Watertight connector assembly;
31. Threaded sleeve;
311. Transverse plate;
32. Silicone annular gasket;
33. Fastening screw;
40. Multi-core cable;
100. Ground acquisition station.

What is claimed is:

1. A single-hole multi-stage pore water pressure observation device, comprising a plurality of digital piezometer probe assemblies arranged at intervals in a monitoring borehole from bottom to top, an inter-stage seepage-isolation cylinder assembly connected between two adjacent digital piezometer probe assemblies of the plurality of digital piezometer probe assemblies, and watertight connector assemblies configured to connect the two adjacent digital piezometer probe assemblies to the inter-stage seepage-isolation cylinder assembly, wherein each of the plurality of digital piezometer probe assemblies comprises a slender hollow water-permeable cylinder, a pore water pressure gauge assembly disposed in the slender hollow water-permeable cylinder, a high-permeability material filled in gaps between an inner wall of the slender hollow water-permeable cylinder and the pore water pressure gauge assembly, and a water-permeable geotextile wrapped around the high-permeability material; and a multi-core cable is electrically connected between adjacent pore water pressure gauge assemblies, and the multi-core cable passes through the inter-stage seepage-isolation cylinder assembly between the adjacent pore water pressure gauge assemblies.

2. The single-hole multi-stage pore water pressure observation device according to claim 1, wherein the inter-stage seepage-isolation cylinder assembly comprises one section of seepage-isolation cylinder or a plurality of sections of seepage-isolation cylinders connected in series;

each seepage-isolation cylinder comprises a central tube and a grid cage which are concentrically arranged from inside to outside, and a water-swellable material wrapped in a water-soluble film is filled between the central tube and the grid cage; and the multi-core cable extends out from both ends of the central tube and is connected to the adjacent pore water pressure gauge assemblies, respectively.

3. The single-hole multi-stage pore water pressure observation device according to claim 2, wherein the plurality of digital piezometer probe assemblies, the seepage-isolation cylinder and the watertight connector assemblies are all integrally prefabricated.

4. An installation method for the single-hole multi-stage pore water pressure observation device according to claim 2, comprising the following steps:

according to observation design requirements, deploying a drilling rig to drill a borehole at a site to be tested, and using a drilling casing to protect a borehole wall; and when the borehole is drilled to a depth that is deeper than a designed depth by a length of one section of inter-stage seepage-isolation cylinder, pulling out a drill pipe, erecting a temporary work platform near a borehole opening, and preparing equipment and materials for installation of the single-hole multi-stage pore water pressure observation device;

transporting a corresponding number of the plurality of digital piezometer probe assemblies, sections of the seepage-isolation cylinders, and the watertight connector assemblies to the site according to monitoring design requirements;

before embedding, soaking all of the plurality of digital piezometer probe assemblies in clean water for more than 24 h to expel air from probes inside the plurality of digital piezometer probe assemblies;

before embedding, assembling the seepage-isolation cylinders in each inter-stage seepage-isolation cylinder assembly on ground, and connecting two adjacent seepage-isolation cylinders through a watertight connector assembly;

using a stage-by-stage installation method, placing a first-stage inter-stage seepage-isolation cylinder assembly into a monitoring borehole and connecting a first-stage digital piezometer probe assembly of the plurality of digital piezometer probe assemblies to an upper end of the first-stage inter-stage seepage-isolation cylinder assembly through the watertight connector assembly; then placing a second-stage inter-stage seepage-isolation cylinder assembly into the monitoring borehole and connecting the second-stage inter-stage seepage-isolation cylinder assembly to an upper end of the first-stage digital piezometer probe assembly through the watertight connector assembly; and continuing assembly in sequence until all of the plurality of digital piezometer probe assemblies, inter-stage seepage-isolation cylinder assemblies and watertight connector assemblies are placed into the borehole;

installing a ground acquisition station, and commissioning and testing working status of probes of the plurality of digital piezometer probe assemblies at all stages and an integrity of data transmission; and lifting the drilling casing out of the borehole and fully filling the borehole with water; and by using the water-swellable material that swells upon contact with water, forming a borehole sealing layer between the plurality of digital piezometer probe assemblies at the stages, thereby achieving mutual isolation of water pressures in formations where the plurality of digital piezometer probe assemblies at the stages are located, preventing vertical communication and mutual seepage between the pore water pressure gauge assemblies at the stages.

5. The single-hole multi-stage pore water pressure observation device according to claim 2, wherein the pore water pressure gauge assembly comprises a package housing, a small locknut, a large locknut, an acquisition circuit board, a pore water pressure sensor and a signal wire thereof that are electrically connected to the acquisition circuit board, and a probe multi-core cable electrically connected to the acquisition circuit board; and part of the probe multi-core cable, the signal wire, and the acquisition circuit board are all located within the package housing; the small locknut is configured to seal off a part where the signal wire extends out of the package housing; and the large locknut is configured to seal off a part where the probe multi-core cable extends out of the package housing.

6. The single-hole multi-stage pore water pressure observation device according to claim 5, wherein the acquisition circuit board comprises:

a microcontroller unit (MCU) integrated with a storage module;

an excitation and frequency sweeping module, a signal processing module and a temperature acquisition module which are all electrically connected to the MCU; and a bus communication module and a power supply module which are both electrically connected to the MCU; and the pore water pressure sensor is electrically connected to the excitation and frequency sweeping module, the signal processing module and the temperature acquisition module.

7. The single-hole multi-stage pore water pressure observation device according to claim 5, wherein the high-permeability material is medium-coarse sand, the water-swellable material is water-swellable resin, and the acquisition circuit board is externally sealed and encapsulated with epoxy resin.

8. The single-hole multi-stage pore water pressure observation device according to claim 2, wherein a side wall of the slender hollow water-permeable cylinder is defined with a plurality of water-permeable holes, and upper and lower ends of the slender hollow water-permeable cylinder are provided with cylinder covers, each of the cylinder covers being provided with an adapter tube configured to be connected to a first end of a watertight connector assembly; and the multi-core cable connected to the pore water pressure gauge assembly sequentially passes through the adapter tube and extends into the inter-stage seepage-isolation cylinder assembly, and an inner wall of the adapter tube is provided with potting adhesive.

9. The single-hole multi-stage pore water pressure observation device according to claim 8, wherein the watertight connector assembly comprises a threaded sleeve with upper and lower openings and silicone annular gaskets;

the threaded sleeve is internally provided with a transverse plate which divides the threaded sleeve into an upper chamber and a lower chamber, with a hole being formed at a center of the transverse plate to allow the multi-core cable to pass through; and the silicone annular gaskets are laid on both sides of the transverse plate respectively, and the upper chamber and the lower chamber on both sides of the transverse plate are respectively configured for threaded connection with the adapter tube and the inter-stage seepage-isolation cylinder assembly.

10. The single-hole multi-stage pore water pressure observation device according to claim 9, wherein in a case where the inter-stage seepage-isolation cylinder assembly comprises the plurality of sections of seepage-isolation cylinders connected in series, the watertight connector assembly is connected between the seepage-isolation cylinders; and the watertight connector assembly further comprises a fastening screw, and the threaded sleeve is defined with a threaded hole corresponding to the fastening screw.

* * * * *